United States Patent [19]

Jackson

[11] 4,159,952
[45] Jul. 3, 1979

[54] POWDERED HYDRATED EMULSIFIERS AND THEIR METHOD OF PREPARATION

[75] Inventor: Clifford A. Jackson, Sanford, Fla.

[73] Assignee: Southland Corporation, Dallas, Tex.

[21] Appl. No.: 862,908

[22] Filed: Dec. 21, 1977

[51] Int. Cl.² .............................................. B01F 17/34
[52] U.S. Cl. ................................. 252/356; 426/654
[58] Field of Search ........................ 252/356; 426/654

[56] References Cited
U.S. PATENT DOCUMENTS

| | | | |
|---|---|---|---|
| 3,623,887 | 11/1971 | Buddemeyer et al. | 252/356 X |
| 3,671,459 | 6/1972 | Norris | 252/356 |
| 3,702,307 | 11/1972 | Norris | 252/356 |
| 3,785,993 | 1/1974 | Langhans | 252/356 |
| 3,993,580 | 11/1976 | Galusky | 252/356 X |

Primary Examiner—Benjamin R. Padgett
Assistant Examiner—E. Suzanne Parr
Attorney, Agent, or Firm—Duckworth, Hobby, Allen & Pettis

[57] ABSTRACT

Unique powdered hydrated emulsifiers, or surfactants, for use in the food and cosmetic industries comprising, by weight, 85–98% emulsifier and 2–15% water. Virtually all of the common emulsifiers capable of hydrogen bonding are suitable for use in preparing the powdered hydrated emulsifier compositions of the present invention. The invention further comprises a method for preparing the powdered hydrated emulsifiers basically comprising a mixing and spray-chilling operation.

10 Claims, No Drawings

4,159,952

POWDERED HYDRATED EMULSIFIERS AND THEIR METHOD OF PREPARATION

BACKGROUND OF THE INVENTION

1. Field of the Invention

The present invention relates to a method for the preparation of powdered hydrated emulsifiers commonly used in the food and cosmetic industries and to the emulsifier compositions themselves.

2. Description of the Prior Art

Surface active agents (emulsifiers) are commonly utilized in the food and cosmetic industries for stablizing and thereby enhancing the physical characteristics of various bakery products, cake icings, shortenings, whipped toppings, and cosmetics. Currently, these emulsifiers are commercially available as powders, plastics or hydrates. As is to be expected, each of these three forms has certain advantages and disadvantages with regard to their handling characteristics and functionalities.

While powdered emulsifiers are most easily handled, they are most difficult to disperse in aqueous and use applications. Accordingly, while easier to handle, powders are the least functional. At the other end of the spectrum are the hydrated emulsifiers. The hydrated emulsifiers offer the best functionality in terms of being readily dispersed in aqueous systems, but are considered extremely inconvenient or messy to handle. The plastic emulsifiers might be termed the "happy medium" of the state of the art. Being semi-solid the plastic emulsifiers are slightly more difficult to handle than the powders, but they do not exhibit the functionality of the hydrates.

Accordingly, it is an object of the present invention to provide a method for the formation of "minimal hydrates" of emulsifier compositions. Another object of the present invention is the powdered hydrated emulsifier compositions themselves. The term "minimal hydrates" refers to the preparation of mixtures of emulsifiers and water that will yield powdered products exhibiting characteristics of functionality approaching those of the fully hydrated emulsifiers which are commercially available today. As stated above, it is, of course, known in the art that to hydrate the emulsifier composition will increase its functionality.

In this regard attention is invited to U.S. Pat. No. 3,702,307 to Norris. Therein a hydrated emulsifier composition is disclosed, but that patent specifically teaches that when the water content falls below about 22% by weight, the emulsifier becomes dysfunctional. In similar fashion U.S. Pat. No. 3,671,459 to Norris teaches that when less than 30% by weight of the emulsifier composition is used for hydration a loss of plasticity and functionality of the emulsifier often results. In fact, that patent teaches that the water content of the hydrated emulsifier should be between about 45 and 55% in order to achieve acceptable results. A similar teaching of a water content of from 20-80% by weight is found in U.S. Pat. No. 3,993,580 to Galusky. In fact, only a single prior art reference has been discovered wherein less than 20% by weight water is present in the emulsifier composition. However, this teaching, found in U.S. Pat. No. 3,785,993 to Langhans, is directed to a clear *liquid* emulsifier baking composition wherein the water is added to the emulsifier as a clarifier and is but one of many possible clarifiers selected from the group consisting of propylene glycol, water, ethanol and edible oils. This patent to Langhans presents no teaching concerning the use of these clarifiers for the purpose of preparing powdered hydrated emulsifiers.

Accordingly, it is clear that there is a great need in the art not only for powdered hydrated emulsifiers, but also for an economical method of their preparation. The resulting powdered hydrated emulsifiers would exhibit two highly desirable characteristics: first, they would exhibit functionalities approaching those of the hydrates; and second, they would possess handling characteristics typical of the powdered forms.

SUMMARY OF THE INVENTION

The present invention relates to a method of preparation for powdered hydrated emulsifiers suitable for use in the food and cosmetic industries as well as to the powdered hydrated emulsifiers themselves. Accordingly, the present invention comprises a method for the formation of what may be termed "minimal hydrates" of emulsifiers or surfactant compositions. Considerations of functionality of the resulting product primarily determine the upper and lower limits of water of hydration with the upper limit being hydrated emulsifiers which tend to stick together and the lower limit being products which while powders exhibit no increased functionality. As will be set forth in greater detail below, the minimal hydrates of the present invention generally consist essentially of 2–15% by weight water.

The principal emulsifiers in use today, and those to which the method and composition of the present invention are directed, are monoglycerides, ethoxylated mono-diglycerides, succinylated monoglycerides, sodium stearoly 2 lactylate, and polyoxyethylene sorbitan monostearate. However, actual test data indicates that virtually all of the common surfactants capable of hydrogen bonding are theoretically capable of forming these "minimal hydrates" either individually or in combination with one or more of the other surfactants/emulsifiers.

The procedure for preparing the powdered hydrated emulsifiers of this invention is first to melt the chosen emulsifier or mixture of emulsifiers, which is usually in a temperature range of from 120°–170° F. The melted emulsifier is then pumped through a conduit to a spray nozzle which communicates with a cooling chamber maintained at about 60° F. Just upstream of the spray nozzle water is metered into the flow of melted emulsifier so that the water/emulsifier mixture exits the spray nozzle into the cooling chamber. The water is maintained at a temperature above about 100° F. The flow of water is metered such that the resulting spray chilled product contained from 2–15% by weight water of hydration. The resulting free flowing powder comprises the powdered hydrated emulsifier composition of this invention, more specific examples of which are presented hereinafter.

While not intending to be bound by this theory, it is believed that spray chilling of these minimal hydrates creates a matrix of water and emulsifier wherein the water is bound to the emulsifier by hydrogen bonding. It is believed that the spraying process first makes an intimate mixture of water and emulsifier and secondly locks the water of hydration into the system by rapid chilling. This theory is supported by the fact that as the particle size of the spray decreases, the limiting water content increases as does the functionality of the powdered hydrated emulsifier composition.

An additional consideration as to the physical and chemical nature of these minimal hydrates is that these emulsifier/water blends can exist in several phases depending upon the temperature and amount of water present. A discussion of these various phases with regard to distilled monoglycerides in aqueous systems is presented in two articles found in chemical literature. The first is by Krog & Larsson, "Phase Behavior and Rheological Properties of Aqueous Systems of Industrial Distilled Monoglycerides," 2 CHEM. PHYS. LIPIDS 129-143(1968). The second is Krog & Borup, "Swelling Behavior of Lamellar Phases of Saturated Monoglycerides in Aqueous Systems," 24 J. SCI. FD AGRIC. 691-701(1973). For example, the Krog & Larsson article presents a diagram of distilled monoglyceride and water showing that in the range of 2-15% by weight water there are three potential phases for the blend; fluid isotropic, neat, or crystals and water. The crystals and water phase would correspond to present commercially available powdered product added to water. At this time, it has not been determined whether the "minimal hydrates" of this invention are locked into the fluid isotropic or into the neat phase. It is even contemplated that the composition of this invention may involve a new phase altogether.

As will be set forth in greater detail below, the powdered hydrated emulsifier compositions of the present invention are utilized in the preparation of food and cosmetic end products in accord with standard procedures of the industries.

The invention accordingly comprises several steps in the relation of one or more of such steps with respect to each of the others, and the composition possessing the features, properties and the relation of constituents which are exemplified in the following detailed disclosure, and the scope of the invention will be indicated in the claims.

DETAILED DESCRIPTION

The present invention relates to a powdered hydrated emulsifier, or surfactant, compositions such as are commonly used in the food and cosmetic industries as well as the manner of preparing said compositions. The method of preparation basically comprises the steps of injecting heated water into a stream of melted emulsifier and spray chilling the resultant mixture to obtain the desired powdered hydrated emulsifiers. The composition of this invention consists essentially of, by weight, 85-98% emulsifier and 2-15% water.

Virtually all of the common emulsifiers capable of hydrogen bonding are suitable for use in the method of the present invention for the purpose of forming the powdered hydrated emulsifier compositions. Accordingly, the emulsifiers utilized in the method and composition of this invention may be defined as consisting of fatty acid partial esters of polyhydric alcohols, half esters of succinic acid of a mono-acylated polyalcohol, alkoxylated condensates of monoglycerides, stearoyl 2 lactylate and calcium and sodium salts thereof, alkoxylated fatty acid partial esters of polyhydric alcohol, diacetyl tartaric acid esters of fatty acid partial esters of polyhydric alcohols, and mixtures of these emulsifiers.

The following examples, then, are set forth in order to fully describe the method and the composition of the present invention.

EXAMPLE 1

One mole of industrial distilled monoglyceride, made from fully hydrongenated fatty acid glycerol esters (principally $C_{16}$ and $C_{18}$), containing 90% alpha monoglyceride, was reacted with one half mole of succinic anhydride. The mixture was melted and heated with stirring until maximum formation of the succinic half ester was formed. One mole of water was added to the succinic half ester and the mixture was sprayed through a spray nozzle into a cooling chamber. The exit spray was therein cooled from about 170° F. to about 60° F.

The resulting cooled product was a free flowing white powder, about 50% of said powder passing through a standard 20 mesh screen. This product contained about 4% by weight water.

The self-emulsification properties of the hydrated powder were examined by placing about 40 grams of the screened material into about 120 grams of water maintained at about 72° F. The mixture was stirred just sufficiently to disperse the powder in the water. The mixture was then observed with no further mixing.

After approximately ten minutes, noticable swelling of the powder had absorbed virtually all of the free water although spherical particles could still be observed. After one hour self-emulsification had occured such that all of the excess water had been absorbed and the spherical nature of the original powder particles could no longer be observed.

In the method for preparing the powdered hydrated emulsifier composition of this Example I, it should be noted that the water was injected into the stream of melted succinic half ester at a point just upstream of the spray nozzle. Experimentation has revealed that if the water is injected into the emulsifier well upstream of the spray nozzle a gel will form. which is not sprayable.

Further examples of the powdered hydrated emulsifier compositions of the present invention were prepared in accord with the spray chilling method of Example I. The resulting powdered hydrated emulsifier compositions thus prepared are presented below. All composition constituents are listed in weight percents.

EXAMPLE II

Succinic half ester of glycerol monoesters: 61%
Glycerol alpha monoesters(90% alpha monoester): 31%
Water: 8%

EXAMPLE III

Saturated mono and diglycerides(54% alpha monoester): 53.4%
Polyoxyethylene mono and diglycerides: 35.6%
Water: 11.0%

EXAMPLE IV

Mono and diglycerides(90% alpha monoester): 61%
Sodium stearoyl 2 lactylate: 31%
Water: 8%

EXAMPLE V

Mono and diglycerides(54% alpha monoester): 75%
Polyoxyethylene sorbitan esters: 19%
Water: 6%

EXAMPLE VI

Diacetyl tartaric acid ester: 50%
Distilled monoglyceride(90% alpha monoester): 41%
Water: 9%

The following examples are given in order to illustrate methods of utilizing the powdered hydrated emulsifier compositions of this invention.

EXAMPLE VII

Industrial type white bread was prepared by the conventional sponge and dough method. Powdered hydrated emulsifier composition of Example I was used as the emulsifying agent. The agent was utilized at 0.25%, 0.31% and 0.37% levels, said amounts being expressed in bakers percent. It should be noted that in the food industry bakers percent relates each of the ingredients to the total amount of flour utilized. The bread formula was as follows:

| Sponge | Dough |
|---|---|
| Flour 62.5% | Flour 37.5% |
| Water 46.0% | Water 17.0% |
| Yeast Food .5% | Sugar 7.0% |
| Yeast 2.5% | Shortening 3.0% |
| | Milk Powder 2.0% |
| | Salt 2.0% |
| | Emulsifier .25; .31; .37% |

The test bread showed excellent grain, texture, volume and softness at all three levels of the powdered hydrated emulsifier composition.

EXAMPLE VIII

Industrial type yellow layer cakes were produced using the emulsifier composition of Example II. The emulsifier composition was utilized at levels of 0.13% and 0.065%. The cake mix formula was as follows:

| Ingredient | Parts |
|---|---|
| Shortening | 75 |
| Granulated Sugar | 602 |
| Cake Flour | 550 |
| Milk Powder | 50 |
| Whole Egg Solids | 21 |
| Egg White Solids | 9 |
| Salt | 9 |
| Baking Powder | 35 |
| Water | 546 |
| Emulsifier | 1¼ and 2½ |

The mixes were prepared in a vertical mixer to yield a homogeneous batter. The cakes made with 0.13%(2½ parts) emulsifier were over-emulsified. The cakes made with 0.065% (1¼ parts emulsifier were excellent.

EXAMPLE IX

A typical whipped topping formula was produced utilizing the powdered hydrated emulsifier composition of Example V. The emulsifier was utilized at a 0.5% level. The whipped topping formula was as follows:

| Ingredient | Parts |
|---|---|
| Shortening | 30 |
| Sucrose | 6 |
| Sodium Casinate | 6 |
| Dextrose | 2 |
| Carboxymethyl cellulose | .5 |
| Sodium Citrate | .05 |
| Water | 54.95 |
| Emulsifier | .5 |

The topping produced showed excellent over-run, stability and dryness.

While the above examples have been presented with specific relation to specified products in the food industry, it is to be understood that the method and composition of the claimed invention is not to be limited thereby. The claimed method may be utilized to prepare powdered hydrated emulsifier compositions useful in yeast raised baked goods, non-yeast raised baked goods, dairy products, creamers, cake icings, puddings, mayonnaise, and cosmetics.

It will thus be seen that the objects set forth above, among those made apparent from the preceding description, are efficiently attained and since certain changes may be made in carrying out the above method and in the composition set forth without departing from the scope of the invention, it is intended that all matter contained in the above description shall be interpretted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A method for the preparation of powdered hydrated emulsifiers, said method comprising the steps of:
   a. selecting said emulsifier from the group consisting of fatty acid partial esters of polyhydric alcohols, half esters of succinic acid of a mono-acylated polyalcohol, alkoxylated condensates of monoglycerides, stearoyl 2 lactylate and calcium and sodium salts thereof, alkoxylated fatty acid partial esters of polyhydric alcohols, diacetyl tartaric acid esters of fatty acid partial esters of polyhydric alcohols, and mixtures of said emulsifiers;
   b. heating the emulsifier until melted;
   c. pumping said heated emulsifier through a conduit;
   d. injecting water at a temperature above 100° F. into the stream of said heated emulsifier; and
   e. spraying the water-emulsifier mixture through a spray nozzle into a cooling chamber to obtain said powdered hydrated emulsifiers containing 2-15% by weight water of hydration.

2. A method as in claim 1 further comprising metering said water injection to obtain said powdered hydrated emulsifier.

3. A method as in claim 1 further comprising injecting said water into said heated emulsifier a relatively short distance upstream from said spray nozzle.

4. A powdered hydrated emulsifier composition primarily intended for use in the food and cosmetic industries, said powdered hydrated emulsifier comprising: 85-98% by weight emulsifier selected from the group consisting of fatty acid partial esters of polyhydric alcohols, half esters of succinic acid of a mono-acylated polyalcohol, alkoxylated condensates of monoglycerides, stearoyl 2 lactylate and calcium and sodium salts thereof, alkoxylated fatty acid partial esters of polyhydric alcohols, diacetyl tartaric acid esters of fatty acid partial esters of polyhydric alcohols, and mixtures of said emulsifiers and 2-15% by weight water.

5. A powdered hydrated emulsifier composition as in claim 4 comprising, by weight, 96% succinic half ester of glycerol monoester and 4% water.

6. A powdered hydrated emulsifier composition as in claim 4 comprising, by weight, 61% succinic half ester of glycerol monoester; 31% glycerol alpha monoester; and 8% water.

7. A powdered hydrated emulsifier composition as in claim 4 comprising, by weight, 53.4% saturated mono and diglyceride of which about 54% is alpha monoester; 35.6% polyoxyethylene mono and diglycerides; and 11% water.

8. A powdered hydrated emulsifier composition as in claim 4 comprising, by weight, 61% mono and diglycerides of which about 90% is alpha monoester; 31% sodium stearoyl 2 lactylate; and 8% water.

9. A powdered hydrated emulsifier composition as in claim 4 comprising, by weight, 75% mono and diglycerides of which about 54% is alpha monoester; 19% polyoxyethylene sorbitan ester; and 6% water.

10. A powdered hydrated emulsifier composition as in claim 4 comprising, by weight, 50% diacetyl tartaric acid ester; 41% distilled monoglyceride of which about 90% is alpha monoester; and 9% water.

* * * * *